US011517681B2

(12) United States Patent
Zhang

(10) Patent No.: US 11,517,681 B2
(45) Date of Patent: Dec. 6, 2022

(54) DISPOSABLE INJECTION NEEDLE

(71) Applicant: Tianjin Huahong Technology Co., Ltd., Tianjin (CN)

(72) Inventor: Libo Zhang, Tianjin (CN)

(73) Assignee: TIANJIN HUAHONG TECHNOLOGY CO., LTD., Tianjin (CN)

( * ) Notice: Subject to any disclaimer, the term of this patent is extended or adjusted under 35 U.S.C. 154(b) by 114 days.

(21) Appl. No.: 16/427,665

(22) Filed: May 31, 2019

(65) Prior Publication Data

US 2019/0366013 A1 Dec. 5, 2019

(30) Foreign Application Priority Data

Jun. 1, 2018 (CN) .......................... 201810559376.4

(51) Int. Cl.
*A61M 5/32* (2006.01)
(52) U.S. Cl.
CPC ........ *A61M 5/3204* (2013.01); *A61M 5/3245* (2013.01); *A61M 5/3257* (2013.01); *A61M 5/3271* (2013.01)
(58) Field of Classification Search
CPC .............. A61M 5/3204; A61M 5/3245; A61M 5/3257; A61M 5/3271; A61M 2005/3247; A61M 2005/3267; A61M 5/3275; A61M 5/3202; A61M 5/321; A61M 2005/3254; A61M 2005/3258; A61M 5/2033; A61M 5/326; A61M 5/3243
See application file for complete search history.

(56) References Cited

U.S. PATENT DOCUMENTS

| 2009/0259178 | A1 | 10/2009 | Brechbuehler et al. |
| 2015/0165123 | A1* | 6/2015 | Thornton .............. A61M 5/282 604/110 |
| 2016/0228654 | A1* | 8/2016 | Rozwadowski ... A61B 10/0233 |
| 2017/0182260 | A1 | 6/2017 | Schraga |

FOREIGN PATENT DOCUMENTS

GB 2542202 A 3/2017

OTHER PUBLICATIONS

Extended European Search Report in Corresponding EP Application No. 19177714.3 dated Oct. 23, 2019. 9 pages.
Office Action and English translation for corresponding Chinese Application No. 201910466699.3, dated Jun. 22, 2021. 22 pages.

* cited by examiner

*Primary Examiner* — Lauren P Farrar
(74) *Attorney, Agent, or Firm* — Leason Ellis LLP

(57) ABSTRACT

The present disclosure relates to a disposable injection needle including: a needle mount having a tube needle; a first sleeve, one end of which is suitable for connecting to the needle mount to define receiving space, and the other end of which is provided with a first opening; a second sleeve, one end of which is located inside the receiving space, and the other end of which having a second opening; an elastic element adapted to allow the second sleeve moves axially toward outside the receiving space, wherein: the needle mount or the first sleeve is provided with a stop surface and a limit groove; the second sleeve is provided with a limit arm comprising a limit face and a protruding member which is adapted to enter the limit groove with axial relative movement between the first sleeve and the second sleeve.

17 Claims, 9 Drawing Sheets

A—A

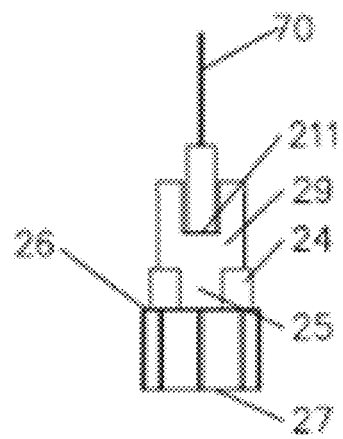
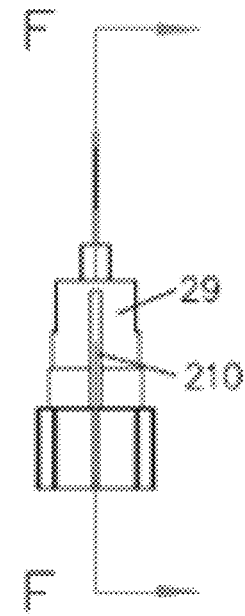
Fig. 2a　　　　　　　　Fig. 2b
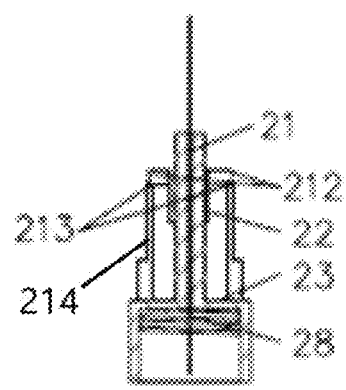
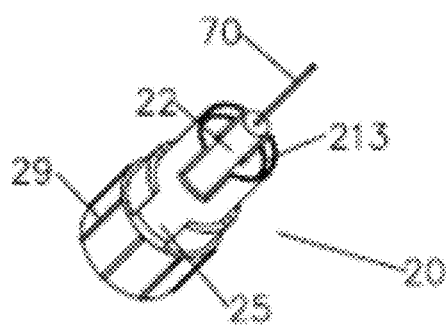
F—F
Fig. 2c　　　　　　　　Fig. 2d

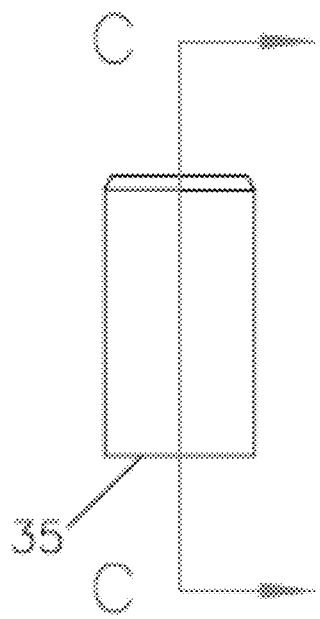
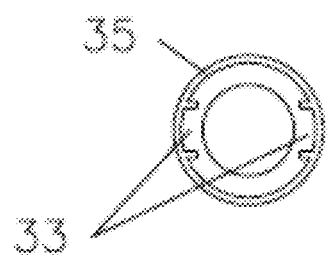
Fig. 3a	Fig. 3b
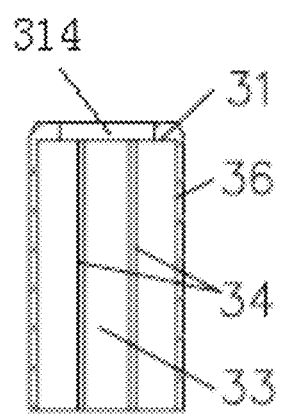
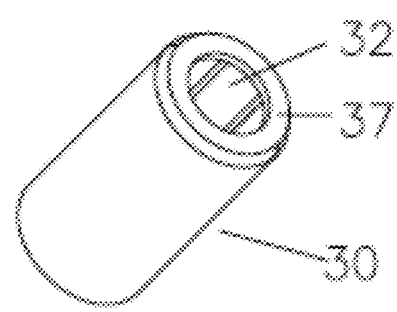
Fig. 3c	Fig. 3d

D—D

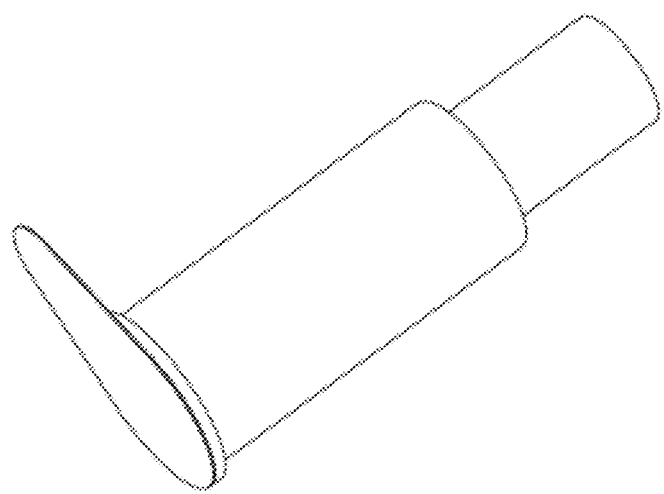
Fig. 8
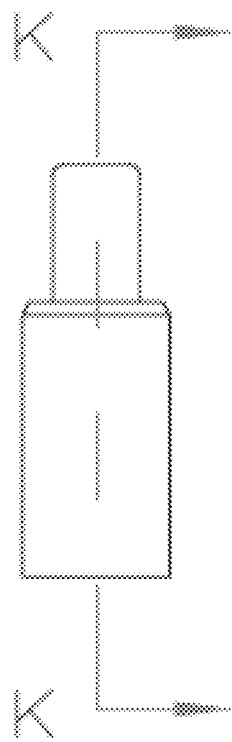
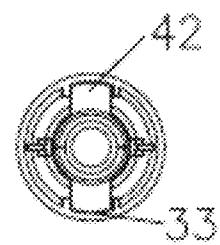
Fig. 9a          Fig. 9b

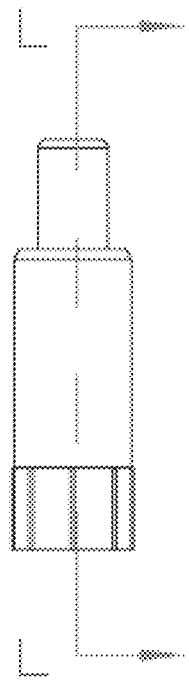
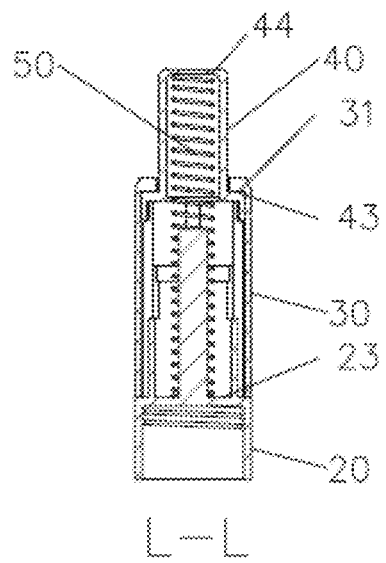
Fig. 10b    Fig. 10c
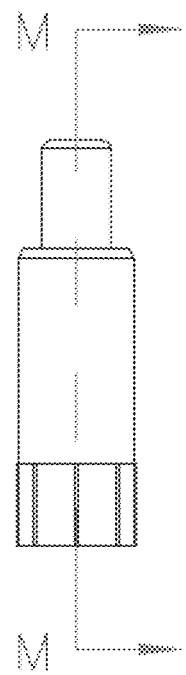
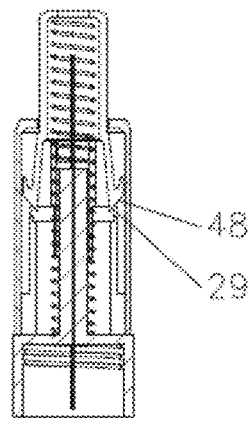
Fig. 11a    Fig. 11b

ID:00015

DISPOSABLE INJECTION NEEDLE

CROSS-REFERENCE TO RELATED PATENT APPLICATIONS

This application is claims the benefit of priority of Chinese Patent Application number 201810559376.4 filed Jun. 1, 2018, which is incorporated by reference in its entirety.

TECHNICAL FIELD

The embodiment of the present disclosure relates to the field of medical instruments, more particularly, to a disposable injection needle.

BACKGROUND

A conventional injection needle, which is common in the market and cooperates with an insulin injection pen, comprises a big sleeve, a small sleeve, a needle mount, a tube needle and dialyzing paper. The needle tip of the tube needle will be exposed all the time once the big sleeve and the small sleeve are removed, which increases the infection probability for the patients because of secondary use, and the used needle is apt to accidentally injure other people and thus causes cross-infection.

In addition, the big sleeve tends to slide outside the needle mount when the injection needle is being engaged with the injection pen, leading to poor working conditions, for instance unstable assembling.

SUMMARY

The present disclosure is proposed to alleviate or solve at least one aspect of the above problems.

According to one aspect of the embodiment in the present disclosure, the present disclosure provides a disposable injection needle, which comprises:

a needle mount provided with a tube needle that extends axially therethrough;

a first sleeve, one end of which is suitable for connecting to one end of the needle mount to form receiving space between the first sleeve and the needle mount, and the other end of the first sleeve is provided with a first opening;

a second sleeve, one end of which is located inside the receiving space, and the other end of which having a second opening, extends out from the first opening, wherein part of the second sleeve is provided in an axially slideable manner inside the receiving space, and the tube needle is adapted to protrude through the second opening;

an elastic element adapted to provide elastic force for the second sleeve to move axially toward outside the receiving space, and the second sleeve is adapted to retract inward the receiving space based on an external force overcoming the elastic force, so as to expose the tube needle, wherein:

the needle mount or the first sleeve is provided with a stop surface and a limit groove;

the second sleeve is provided with a limit arm comprising a limit face and a protruding member which protrudes radially, the protruding member is adapted to enter the limit groove with axial relative movement between the first sleeve and the second sleeve;

the limit face has a first radial location and a second radial location, the location of the limit face is adapted to be changed radially based on elastic deformation of the limit arm, and the limit face is in the second radial location in the case that the protruding member is in the limit groove;

in the first radial location, the limit face is adapted to pass axially the stop surface, and in the second radial location, the limit face is adapted to abut against the stop surface to prevent the second sleeve from moving axially further toward inside the receiving space.

Alternatively, the limit groove extends axially; and the protruding member is a fastener which is adapted to hook or abut against one end of the limit groove when the protruding member in the limit groove moves toward the first opening.

Alternatively, the end of the limit arm has a limit block and the fastener, wherein the fastener protrudes radially outward, the limit block extends circumferentially or substantially circumferentially on both sides of the fastener, the end face of the limit block in the axial direction constitutes the limit face, and the limit face is located outside the limit groove in the case that the fastener is in the limit groove.

Alternatively, the second sleeve is further provided with a guiding portion, the needle mount and/or first sleeve is provided with a guiding engagement portion, wherein the guiding portion engages with the guiding engagement portion to guide the axial movement of the second sleeve.

Alternatively, the stop surface comprises a step surface which is perpendicular to the axis and extends radially.

Alternatively, the needle mount is provided with an engaging cylinder, and the engaging cylinder includes a body portion and an edge portion, the step surface is formed at the junction therebetween. Further alternatively, the body portion of the engaging cylinder is provided with the limit groove.

Alternatively, the limit arm is adapted to deform radially inwardly when being pressed by the internal face of the engaging cylinder or by the inner wall of the first sleeve.

Alternatively, the protruding member is a fastener which is provided with a pressing slope, which extends obliquely outward in the radial direction from the end of the fastener. Furthermore, the fastener is further provided with a pressing side-face, which extends axially from the end of the pressing slope to the second opening. Furthermore, the pressing side-face and the body of the limit arm forms a hook which hooks one end of the limit groove when the fastener moves toward the first opening.

Alternatively, the guiding portion of the second sleeve extends radially outward from the body of the second sleeve; the inner wall of the first sleeve is provided with a guiding slot, which guides the axial movement of the guiding portion, the guiding engagement portion includes the guiding slot. Further, the needle mount is further provided with an engaging notch extending axially, which the guide slot extends into or enters when the first sleeve is sleeve-jointed to the needle mount, and the guiding engagement portion further includes the engaging notch. Or further, the first sleeve has a first blocking face which defines the first opening; the guiding portion of the second sleeve has a second blocking face which is adapted to abut against the first blocking face of the first sleeve.

Alternatively, the inner wall of the first sleeve are provided with the stop surface and the limit groove, or the first sleeve is provided with the limit groove and the needle mount is provided with the stop surface; the stop surface is closer to the first opening than the limit groove.

Alternatively, the disposable injection needle further includes a third sleeve which sleeve-joints the needle mount, the first sleeve and the second sleeve from outside. Further, a first anti-rotational mechanism is provided between the first sleeve and the needle mount, and a second anti-rotational mechanism is provided between the third sleeve and the needle mount.

Alternatively, the second sleeve is provided with two guiding portions and two limit arms, wherein the two limit arms are arranged to be opposite to each other in the radial direction, and the two guiding portions are arranged to be opposite to each other in the radial direction.

According to the embodiment of the present disclosure, with the internal structure design of the injection needle assembly, the needle tip of the tube needle will not be exposed to the outside after being used.

BRIEF DESCRIPTION OF DRAWINGS

FIGS. 2a, 2b, 2c, 2d, are respectively a front view, a left view, a sectional view and a stereoscopic view of the needle mount according to one exemplary embodiment of the present disclosure;

FIGS. 3a, 3b, 3c, 3d, are respectively a front view, an upward view, a sectional view and a stereoscopic view of the auxiliary sleeve (the first sleeve) according to one exemplary embodiment of the present disclosure;

FIG. 8 is a stereoscopic view of the injection needle according to one exemplary embodiment of the present disclosure.

FIGS. 9a, 9b, 9c, 9d are respectively a front view, an upward view, a sectional view and a stereoscopic view of the sleeve assembly according to one exemplary embodiment of the present disclosure.

FIGS. 10a, 10b, 10c are respectively a stereoscopic view, a front view, and a sectional view of the injection needle whose big sleeve has been removed and which just contacts with user's skin, according to one exemplary embodiment of the present disclosure.

FIGS. 11a, 11b are respectively a front view and a sectional view of the injection needle whose big sleeve has been removed, piercing into user's skin and the M-M showing the spring state according to one exemplary embodiment of the present disclosure.

DETAILED DESCRIPTION OF PREFERRED EMBODIMENTS

Figure 1A:
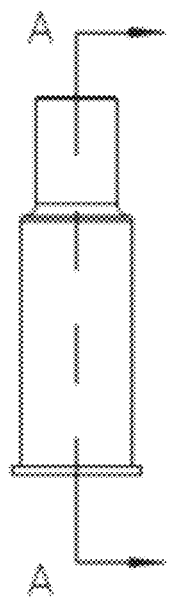
FIGS. 1a, 1b, 1c, 1d are respectively a front view, an upward view, a sectional view and a stereoscopic view of the big sleeve (the third sleeve) according to one exemplary embodiment of the present disclosure.
Figure 1B:
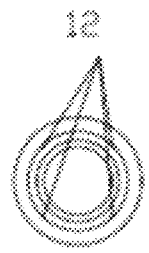
Figure 1C:
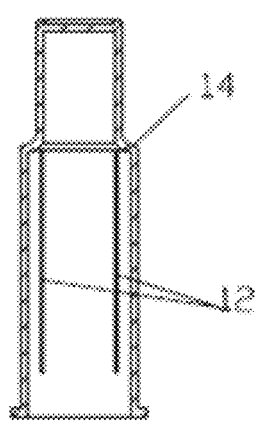
Figure 1D:
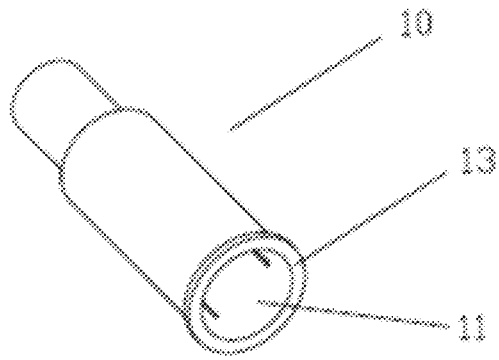
Figure 4A:
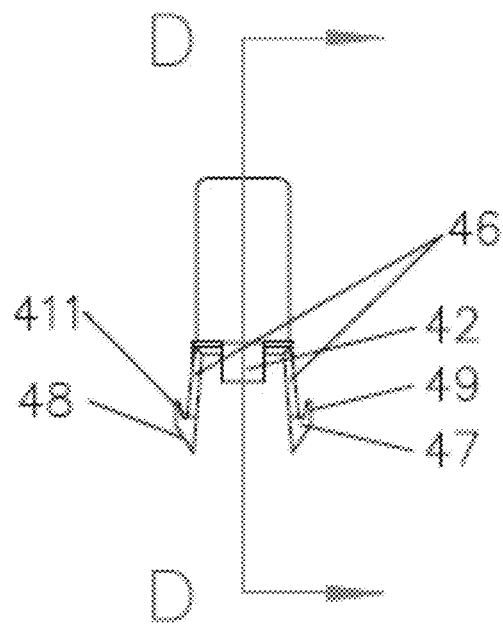
FIGS. 4a, 4b, 4c, 4d, 4e, 4f are respectively a front view, an upward view, a vertical view, a sectional view, a left view and a stereoscopic view of the small sleeve (the second sleeve) according to one exemplary embodiment of the present disclosure.
Figure 4B:
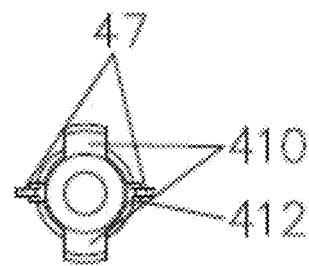
Figure 4C:
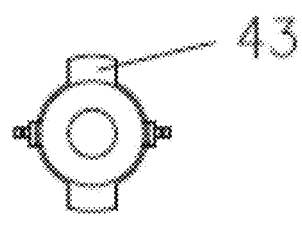
Figure 4D:
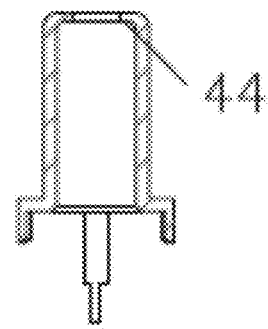
Figure 4E:
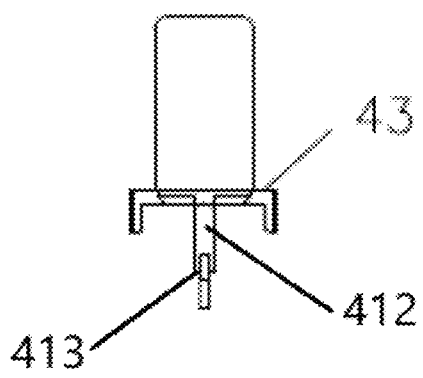
Figure 4F:
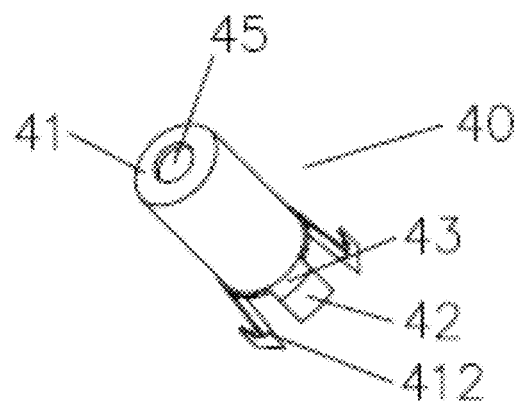

The technical solutions of the present disclosure will be further described below, with reference to the embodiments and the accompanying drawings. In the specification, the same or analogous drawings reference numerals indicate the same or analogous components. The following explanation of the present disclosure embodiment, with reference to attached drawing, is intended to explain the inventive concept of the present disclosure and should not be understood as a limitation to the present disclosure.

Figure 5:
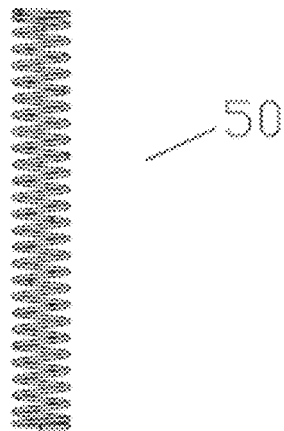
FIG. 5 shows an elastic element according to one exemplary embodiment of the present disclosure.
Figure 6:
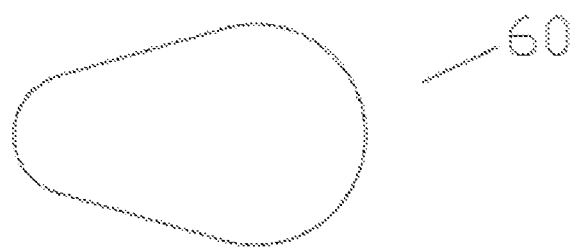
FIG. 6 is a front view of the dialyzing paper according to one exemplary embodiment of the present disclosure.
Figure 7A:
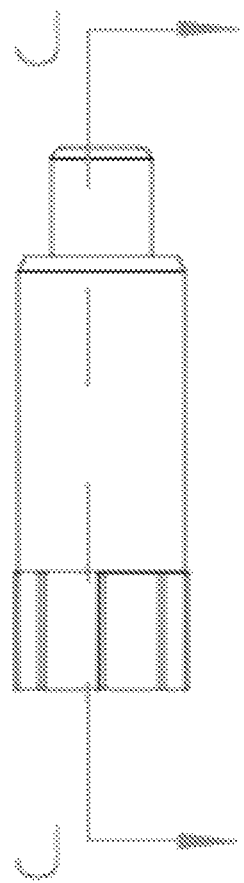
FIGS. 7a, 7b are respectively a front view and a sectional view of the injection needle without the big sleeve according to one exemplary embodiment of the present disclosure.
Figure 7B:
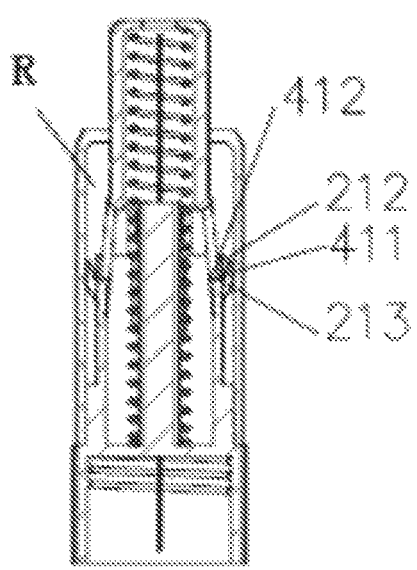
Figure 9C:
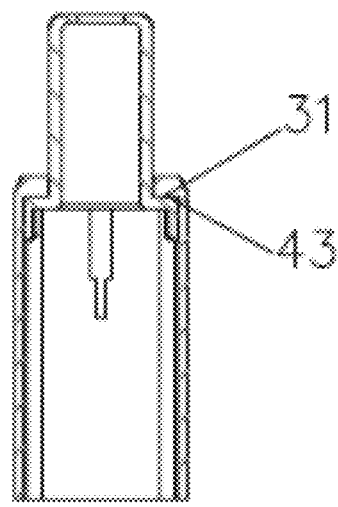
Figure 9D:
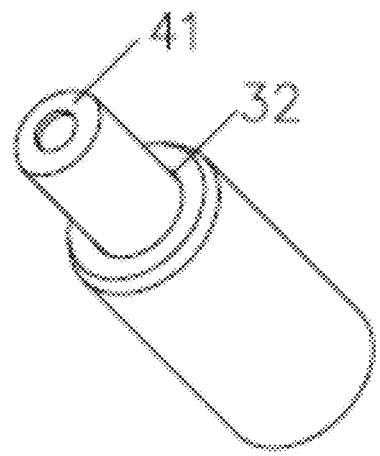

Firstly, with reference to the drawings, the injection needle, according to one exemplary embodiment of the present disclosure, is described in detail, and it is noted that that, for the sake of clarity, some features or elements in the figures are not specifically illustrated. As shown in the figures, the injection needle, according to one exemplary embodiment of the present disclosure, comprises:

a needle mount 20, as shown in FIGS. 2a-2d, is provided with a tube needle 70 extending axially therethrough the needle mount 20;

a first sleeve 30, as shown in FIGS. 3a-3d and FIGS. 7a-7b, one end of which is suitable for connecting to one end of the needle mount 20 to form a receiving space R between the first sleeve 30 and the needle mount 20, and the other end of the first sleeve 30 is provided with a first opening 314;

a second sleeve 40, as shown in FIGS. 4a-4f and 7a-7b, one end of which is located inside the receiving space R, and the other end of the second sleeve 40 having a second opening 45, extends out from the first opening 314, and part of the second sleeve 40 is provided in an axially slideable manner inside the receiving space R, and the tube needle 70 is suitable to protrude through the second opening 45;

an elastic element 50 (referring to FIG. 5) which is adapted to provide an elastic force to allow the second sleeve 40 to move axially toward outside the receiving space, wherein the second sleeve 40 is adapted to retract inward the receiving space, based on the external force overcoming the elastic force, so as to expose the tube needle 70, wherein:

referring to FIGS. 4a-4f, FIGS. 9a-9d, the second sleeve 40 is provided with a guiding portion 42, and the first sleeve 30 is provided with a guiding engagement portion 33, the guiding portion 42 engages with the guiding engagement portion 33 to guide the axial movement of the second sleeve;

referring to FIGS. 2a-2d, the needle mount 20 is provided with an engaging cylinder 29 (the cylinder here only shows that cylinder 29 is generally cylindrical, as shown in FIGS. 2a-2d, and the notch can also be provided to the cylinder 29, the bottom of which is provided with the anti-rotating face 211 engaging with the anti-rotating face 410; for another example, in order that the cylinder 29 is elastic and thus may be deformed radially outward, the cylinder 29 may be divided into several arc strips extending axially), and the engaging cylinder 29 comprises an edge portion 212 and a body portion 214, the stop surface 213 is formed at the junction between the edge portion and the body portion on the inner wall of the engaging cylinder 29, the body portion 214 of the engaging cylinder 29 is provided with a limit groove 210 which extends axially;

referring to FIGS. 4a-4f, the second sleeve 40 is provided with a limit arm 46, the end of which has a limit block 412, and a fastener 47 protruding radially outward, wherein the limit block 412 extends circumferentially or substantially circumferentially on the both sides of the fastener 47, the end face of the limit block 412 in the axial direction constitutes the limit face 413;

referring to FIGS. 7a-7b, FIGS. 11a-11b, the engaging cylinder 29 and the limit arm 46 are provided to allow the fastener 47 to enter the limit groove 210 due to the elastic deformation (the elastic deformation herein might be the elastic deformation of the limit arm or that of the cylinder 29);

the fastener 47 is adapted to move inside the limit groove 210, and the limit block 412 is located outside the limit groove 412 in that case;

referring to FIGS. 7a-7b, the limit face is adapted to abut against the stop surface 213 to prevent the second sleeve 40 from moving axially further again toward inside the receiving space, and the fastener 47 is adapted to hook or abut against one end of the limit groove when moving toward the first opening.

Based on the above technical solution, when the second sleeve is pressed, the fastener 47 on the limit arm 46 of the second sleeve enters the engaging cylinder 29 of the needle mount 20, then the fastener 47 enters the limit groove 210 due to the elastic deformation, where the limit face 413 of the limit block 412 does not contact with the stop surface 213 (in other words, the inward axial movement of the second sleeve will not be blocked), and as the second sleeve 40 is pressed further, the fastener 47 moves axially in the limit groove 210 until the injection operation can be carried out. After the injection, the second sleeve 40 is pushed outwards due to the elastic force of the elastic element 50, where since the fastener 47 is adapted to hook one end of the limit groove when moving toward the first opening, the limit arm 46 of the second sleeve 40 cannot be withdrawn to the outside of the engaging cylinder 29, and there is no possibility that the limit arm 46 enters the engaging cylinder 29 again to prevent the limit face 413 from contacting with the stop surface due to elastic deformation; at the same time, because part of the fastener 47 of the limit arm 46 is located inside the limit groove 210, and the deformation of the limit arm 46 or the engaging cylinder 29 is tiny, the limit face is provided to face the stop surface in the axial direction to prevent the second sleeve 40 from moving axially inward.

Though the second sleeve is provided both the limit arm and the guiding portion in the exemplary embodiment, the limit arm and the guiding portion may be the same part, that is, the limit arm may be used as the guiding portion.

In the accompanying drawings, the limit groove 210 is a strip-shaped hole penetrating radially the wall of the engaging cylinder. It is noted that, however, the limit groove 210 is not necessarily a penetrating-hole as long as it is deep enough to allow the elastic deformation. For example, the limit groove 210 meets the condition that the elastic deformation of the guiding arm or the engaging cylinder is small when the fastener is inside the limit groove (allowing the limit face to abut against the stop surface), and the elastic deformation is relatively large when the fastener is outside the limit groove and inside the engaging cylinder (avoiding the abutment between the limit face and the stop surface).

In the above embodiment, the fastener engages with the needle mount. In fact, the fastener can also engage with the first sleeve. Specifically, though it is not shown, the inner wall of the first sleeve are provided with the stop surface and the limit groove, and the stop surface is closer to the first opening than the limit groove; the limit arm is arranged to allow the fastener to enter the limit groove due to the elastic deformation of the limit arm. The limit groove can also be formed on the first sleeve, and the stop surface can be formed on the needle mount, where the stop surface can be either the stop surface formed on the inner wall of the needle mount or the end face provided on the end of needle mount. It may also be noted that, the limit arm can also deform radially when pressed by the inner wall of the first sleeve.

Correspondingly, the embodiment of the present disclosure also provides the following technical solution:

a disposable injection needle, including:

a needle mount provided with a tube needle that extends axially therethrough;

a first sleeve, one end of which is suitable for connecting to one end of the needle mount to form a receiving space between the first sleeve and the needle mount, and the other end of the first sleeve is provided with the first opening;

a second sleeve, one end of which is located inside the receiving space, and the other end of which having a second opening, extends out from the first opening, wherein part of the second sleeve is provided in an axially slideable manner inside the receiving space, and the tube needle is adapted to protrude through the second opening;

an elastic element, which is adapted to provide elastic force for the second sleeve moves axially toward outside the receiving space, and the second sleeve is adapted to retract inward the receiving space based on an external force overcoming the elastic force, so as to expose the tube needle, wherein:

the needle mount or the first sleeve is provided with a stop surface and a limit groove;

the second sleeve is provided with a limit arm comprising a limit face and a protruding member which protrudes radially, the protruding member is adapted to enter the limit groove with axial relative movement between the first sleeve and the second sleeve;

the limit face has a first radial location and a second radial location, the location of the limit face is adapted to be changed radially based on elastic deformation of the limit arm, and the limit face is in the second radial location in the case that the protruding member is in the limit groove;

in the first radial location, the limit face is adapted to pass axially the stop surface, and in the second radial location, the limit face is adapted to abut against the stop surface to prevent the second sleeve from moving axially further toward inside the receiving space.

The technical solution of embodiment of the present disclosure is further illustrated with reference to the accompanying drawings.

As shown in the Figures, in an alternative embodiment, the second sleeve 40 is provided with two guiding portions 42 and two limit arms 46, wherein the two limit arms 46 are provided to be opposite to each other in the radial direction and the two guiding portions 42 are provided to be opposite to each other in the radial direction. As known to those of ordinary skill in the art, the fitting configuration on the first sleeve and the needle mount is correspondingly arranged.

In the embodiment shown in the drawings, the limit arm deforms elastically, that is, the limit arm is adapted to deform radially inward when being pressed by the inner wall of the engaging cylinder. However, in an alternative embodiment of the present disclosure, the engaging cylinder can deform elastically, that is, the engaging cylinder deforms radially outward when being pressed by the fastener.

As shown in FIGS. 4a-4f, the fastener 47 is provided with a pressing slope 48 which extends obliquely outward in the radial direction from the end of the fastener.

In a further alternative embodiment, as shown in FIGS. 4a-4f, the fastener 47 is further provided with a pressing side-face 49 which axially extends from the end of the pressing slope toward the second opening.

As shown in FIGS. 4a-4f and FIGS. 7a-7b, the pressing side-face 49 and the body of the limit arm form a hook which hooks one end of the limit groove 210 when the fastener 47 moves toward the first opening.

As shown in FIGS. 4a-4f, the guiding portion 42 of the second sleeve 40 extends radially outward from the body of the second sleeve; as shown in FIGS. 3a-3d, the guiding engagement portion 33 is provided on the inner wall of the first sleeve 30 and is a guiding slot to guide the axial movement of the guiding portion 42. Further, as shown in FIGS. 2a-2f, the needle mount 20 is further provided with an engaging notch 25 extending axially, into which the guiding slot extends or enters, where the first sleeve 30 is sleeve-jointed to the needle mount 20.

As shown in FIGS. 3a-3d, the first sleeve 30 has a first blocking face 31 which defines the first opening 32; as shown in FIGS. 4a-4f, the guiding portion 42 of the second sleeve 40 has a second blocking face 43 which is adapted to abut against the first blocking face 31 of the first sleeve.

The following is the illustration of the installation of the elastic element 50. As shown in FIGS. 2a-2d and FIG. 7b, in the embodiment of the present disclosure, the first end of the needle mount 20 is provided with an elastic element limiting column 22, extending axially from the first end of the needle mount 20, and the tube needle 70 extends axially therethrough; as shown in FIGS. 4a-4f and FIG. 10c, the other end of the second sleeve 40 has a third blocking face 44, which is perpendicular to the axis and defines the second opening; the elastic element includes a spring, one end of which is sleeved on the elastic element limiting column 22 and the other end of which presses against the third blocking face 44. It should be pointed out that the elastic element 50 is not necessarily to abut against the end face from which the elastic element limiting column of the needle mount 20 extends, as long as one end of the elastic element can be fixed to the elastic element limiting column. However, in a further embodiment, as shown in FIG. 10c, the elastic element 50 can be relatively loosely sleeve-jointed to the elastic element limiting column 22 so that it can deform along the entire spring span.

In an alternative embodiment of the present disclosure, the elastic element can also be installed by other methods. For example, one end of the elastic element is fixed to the first sleeve and the other end of which can be fixed to the second sleeve, and the elastic element provides the elastic pulling force so that the second sleeve moves axially toward outside the receiving space.

In an alternative embodiment of the present disclosure, the needle further includes a third sleeve 10, which sleeve-joints the needle mount 20, the first sleeve 30 and the second sleeve 40 from outside.

Alternatively, a first anti-rotational mechanism (such as a rib or a protrusion, or interference fitting configuration) is provided at the junction between the first sleeve and the needle mount, and a second anti-rotational mechanism (such as anti-rotating rib 12 or protrusion, or interference fitting configuration) is provided at the junction between the third sleeve and the needle mount.

Alternatively, the needle further includes dialyzing paper 60, which is provided to cover the opening of the third sleeve.

Alternatively, the other end of the needle mount 20 is provided with a connecting device suitable to connect with the injection pen. The connecting device can be a thread 28, as shown in FIGS. 2a-2d.

It should be pointed out that, in the present disclosure, a bar or a rib only differs from each other slightly in size, otherwise, they should be considered as the same, in other words, it could be considered that a bar and a rib have essentially the same meaning in the present disclosure.

Referring to the above structure, the assembling process of the needle, according to one aspect of the embodiment of the present disclosure, is described.

Figure 10A:
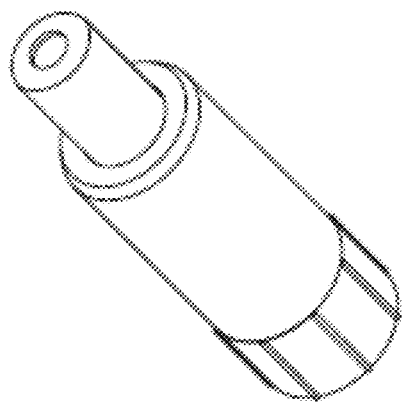

The tube needle 70 is passed through the preset through-hole 21 inside the needle mount 20 to rest on the designated position, then the tube needle 70 and the needle mount 20 are fixed by means such as adhesion; the elastic element 50 is fixed to the elastic element limiting column 22 of the needle mount 20, one end of the elastic element contacts with the elastic element limit face 23 of the needle mount 20, and the inner diameter of the elastic element is slightly greater than the outer diameter of the elastic element limiting column, which ensure that the elastic element presses and extends freely;

the front end face 41 of the small sleeve (corresponding to the second sleeve) faces the end face 35 of the auxiliary sleeve (corresponding to the first sleeve), and it should be ensured that the guiding arm 42 of the small sleeve is aligned with the limit groove of the auxiliary sleeve for the small sleeve (corresponding to the guiding engagement portion 33), then the front end face 41 of the small sleeve is passed through the through-hole of the auxiliary sleeve (corresponding to the first opening 32) until the second blocking face 43 of the small sleeve contacts with the limit face of the auxiliary sleeve (corresponding to a first blocking face 31) for the small sleeve and forms a sleeve assembly, as shown in FIGS. 9a-9d;

then the sleeve assembly is fitted on the needle mount, with the end face 35 of the auxiliary sleeve facing the side of the needle mount without internal thread. The guiding engagement portion 33 of the auxiliary sleeve for the small sleeve is aligned with the engaging face notch 25 on the needle mount, and the distance of the outer sidewalls 34 of the auxiliary sleeve for the small sleeve limit groove is smaller than the width of the notch 25. The small sleeve is sleeve-joined to the needle mount until the end face 35 of the auxiliary sleeve contacts with the limit face 26 of the needle mount for the auxiliary sleeve. Since the outer diameter of the engaging face 24 of the needle mount for the auxiliary sleeve is greater than the inner diameter of the inner wall 36 of the auxiliary sleeve, solid fitting between the needle mount and the auxiliary sleeve is ensured. It should be pointed out that, the limit arm 46 of the small sleeve is provided to extend radially outward, and the outer diameter of the sidewall 49 of the fastener 47 is greater than the inner diameter of the engaging face 29 of the needle mount for the limit arm of the small sleeve, so that the small sleeve cannot freely enter the cavity defined by the engaging face of the needle mount for the limit arm of small sleeve; in the meantime, the other side of the elastic element contacts with the elastic element limit face 44 (corresponding to the third blocking face) of the small sleeve, and the free length of the elastic element is greater than the distance from the elastic element limit face 44 of the small sleeve to the elastic element limit face 23 of the needle mount. The small sleeve is subjected to the restriction of the spring supporting force and the limit face 31 of the auxiliary sleeve for the small sleeve, so that the front end face 41 of the small sleeve will not move axially unless it is pressed by an external force, as shown in FIG. 10a-10c;

the big sleeve (corresponding to the third sleeve 10) is assembled onto the aforementioned assembly, the cavity opening 11 of the big sleeve is positioned to face the front end face 41 of the small sleeve, the aforementioned components are sleeve-joined until the end face 13 of the big sleeve and the end face 27 of the needle mount are in the same plane. Since the distance between the shoulder 14 and the end face 13 of the big sleeve is slightly greater than that between the front end face 37 of the auxiliary sleeve and the end face 27 of the needle mount, the aforementioned assembly can be completely contained in the big sleeve without affecting the engagement between the internal thread 28 in the needle mount cavity and the insulin injection pen; and the big sleeve engaging ribs 29 on the needle mount surface are symmetrical distributed along the central axis, the maximum spacing is slightly greater than the inner diameter of the cavity of the big sleeve, so that the big sleeve assembled is not apt to fall off from the needle mount while it can be easily picked off.

Finally, the dialyzing paper is fixed to the end face 13 of the big sleeve by means of adhesion, etc., as shown in FIG. 8.

Referring to the above structure, the operating process of the injection needle, according to one aspect of the embodiment of the present disclosure, is described.

Firstly, after removing the dialyzing paper, the injection needle is rotated and connected to the injection pen. In order to prevent relative sliding between the big sleeve and the needle mount and the resulted unsolid connection, anti-rotating ribs 12, which interfere with the big sleeve engaging ribs 29 on the needle mount, are provided inside the big sleeve.

Secondly, the big sleeve is removed, the front-end face 41 of the small sleeve is aligned with the injection position of the patient, then the small sleeve retracts toward inside of the auxiliary sleeve at the time of pressing, the tube needle passes through the needle outlet 45 of the small sleeve, the guiding arm 42 of the small sleeve moves axially along the small sleeve guiding engagement portion 33 of the auxiliary sleeve, when the limit arm 46 is being assembled into the assembly, part of the guiding face 48 of the fastener contacts with the limit arm engaging face 29 for the small sleeve, referring to FIG. 11, to guide the radial elastic deformation of the limit arm during the retraction of the small sleeve, and then the sidewall 49 of limit arm fastener retracts inward till the outer diameter thereof is smaller than the inner diameter of the limit arm engaging face 29 of the needle mount; a rectangular through-hole (corresponding to the limit groove) 210, whose width is large enough to receive the fastener 47, is provided to the limit arm engaging face 29. The small sleeve continues to slide inward for a certain distance, when the fastener 47 reaches the through-hole 210, the limit arm 46 recovers to its original shape and the fastener 47 enters the through-hole 210 and moves forward; when the anti-rotating face 410 the small sleeve contacts with the anti-rotating engaging face 211 of the needle mount, the small sleeve stops to retract, the tube needle protrudes to a designated length to facilitate the injection;

then, after the injection, the tube needle is pulled out, the small sleeve restores to its original position supported by the elastic element till the hook portion 411 of the fastener 47 hooks the edge portion 212 of the through-hole 210 of the needle mount, as shown in FIG. 7a-7b; when it comes to the situation of secondary use or inadvertently contact with the front end face 41 of the small sleeve, the edge portion 212 of the needle mount connects with the stop surface 213 of the needle mount, while the small sleeve limit face 412 at the side of the fastener abuts against the stop surface 213, referring to FIG. 7a-7b, to prevent secondary use or accidental injury.

The disposable injection needle of the present disclosure can be used for cooperating with an insulin injection pen for the subcutaneous injection of insulin for the diabetics. As known to those of ordinary skill in the art, the disposable injection needle of the present disclosure can also be used cooperatively with other injection pens or medical instrument.

Though the embodiments of the present disclosure have been shown and described, for those of ordinary skill in the art, it is appreciated that these embodiments can be changed without departing from the principles and spirit of the present disclosure, and the scope of the present disclosure is defined by the appended claims and any and all equivalents thereof.

The invention claimed is:

1. A disposable injection needle, comprising:
   a needle mount provided with a tube needle that extends axially therethrough;
   a first sleeve, one end of which is suitable for connecting to one end of the needle mount to form receiving space between the first sleeve and the needle mount, and the other end of which is provided with a first opening;
   a second sleeve, one end of which is located inside the receiving space, and the other end of which having a second opening extends out from the first opening, wherein part of the second sleeve is provided in an axially slideable manner inside the receiving space, and the tube needle is adapted to protrude through the second opening;
   an elastic element adapted to provide elastic force for the second sleeve to move axially toward outside the receiving space, and the second sleeve is adapted to retract inward the receiving space based on an external force overcoming the elastic force, so as to expose the tube needle,
   wherein:
   the needle mount is provided with a stop surface and a limit groove which extends axially;
   the second sleeve is provided with at least one limit arm comprising a limit face and a protruding member which protrudes radially, the protruding member is adapted to enter the limit groove with axial relative movement between the first sleeve and the second sleeve;
   the limit face has a first radial location and a second radial location, the location of the limit face is adapted to be changed radially based on elastic deformation of the at least one limit arm;
   in the first radial location, the limit face is adapted to pass axially the stop surface, and in the case that the limit face is in the second radial location, the protruding member is in the limit groove and the limit face is adapted to abut against the stop surface to prevent the second sleeve from moving axially further toward inside the receiving space; and
   when the protruding member in the limit groove moves toward the first opening, the protruding member is a fastener which is adapted to hook one end of the limit groove, and the limit face abuts against the stop surface.

2. The disposable injection needle according to claim 1, wherein:
   the end of the at least one limit arm has a limit block and the fastener, wherein the fastener protrudes radially outward, the limit block extends circumferentially or substantially circumferentially on both sides of the fastener, the end face of the limit block in the axial direction constitutes the limit face, and the limit face is located outside the limit groove in the case that the fastener is in the limit groove.

3. The disposable injection needle according to claim 1, wherein: the second sleeve is further provided with at least one guiding portion that extends radially outward from the body of the second sleeve, the first sleeve is provided with a guiding engagement portion on an inner wall of the first sleeve, wherein the at least one guiding portion engages with the guiding engagement portion to guide the axial movement of the second sleeve.

4. The disposable injection needle according to claim 3, wherein:
the at least one guiding portion comprises two guiding portions and the at least one limit arm comprises two limit arms, wherein the two limit arms are arranged to be opposite to each other in the radial direction, and the two guiding portions are arranged to be opposite to each other in the radial direction.

5. The disposable injection needle according to claim 1, wherein:
the stop surface comprises a step surface which is perpendicular to the axis and extends radially.

6. The disposable injection needle according to the claim 5, wherein:
the needle mount is provided with an engaging cylinder which comprises a body portion and an edge portion, the step surface is formed at the junction therebetween.

7. The disposable injection needle according to the claim 6, wherein:
the body portion of the engaging cylinder is provided with the limit groove.

8. The disposable injection needle according to claim 6, wherein: the at least one limit arm is adapted to deform radially inward when pressed by an inner wall of the engaging cylinder or that of the first sleeve.

9. The disposable injection needle according to claim 6, wherein:
the protruding member is a fastener which is provided with a pressing slope which extends obliquely outward in the radial direction from the end of the fastener.

10. The disposable injection needle according to claim 9, wherein:
the fastener is further provided with a pressing side-face which extends axially from the end of the pressing slope to the second opening.

11. The disposable injection needle according to claim 10, wherein:
the limit groove extends axially; and the pressing side-face and the body of the at least one limit arm form a hook which hooks one end of the limit groove when the fastener moves toward the first opening.

12. The disposable injection needle according to claim 3, wherein:
the guiding engagement portion is a guiding slot, which guides the axial movement of the at least one guiding portion.

13. The disposable injection needle according to claim 12, wherein:
the needle mount is further provided with an engaging notch extending axially, which the guiding slot extends into or enters when the first sleeve is sleeve-jointed to the needle mount.

14. The disposable injection needle according to claim 12, wherein:
the first sleeve has a first blocking face which defines the first opening;
the at least one guiding portion of the second sleeve has a second blocking face which is adapted to abut against the first blocking face of the first sleeve.

15. The disposable injection needle according to claim 1, wherein: an inner wall of the first sleeve is provided with the stop surface and the limit groove, or the first sleeve is provided with the limit groove, and the needle mount is provided with the stop surface; the stop surface is closer to the first opening than the limit groove.

16. The disposable injection needle according to claim 1, further comprising:
a third sleeve which sleeve-joints the needle mount, the first sleeve and the second sleeve from outside.

17. The disposable needle according to claim 16, wherein:
a rib, a protrusion, or an interference fitting configuration is provided between the first sleeve and the needle mount to prevent relative rotation therebetween, and an anti-rotating rib, a protrusion, or an interference fitting configuration is provided between the third sleeve and the needle mount to prevent relative rotation therebetween.

* * * * *